United States Patent [19]

Eggers et al.

[11] Patent Number: 5,484,436
[45] Date of Patent: Jan. 16, 1996

[54] BI-POLAR ELECTROSURGICAL INSTRUMENTS AND METHODS OF MAKING

[75] Inventors: Philip E. Eggers, Dublin; Andrew R. Eggers, Ostrander, both of Ohio

[73] Assignee: Hemostatic Surgery Corporation, Georgetown, Cayman Islands

[21] Appl. No.: 265,225

[22] Filed: Jun. 24, 1994

Related U.S. Application Data

[63] Continuation-in-part of Ser. No. 877,703, May 1, 1992, Pat. No. 5,324,289, and a continuation-in-part of Ser. No. 877,704, May 1, 1992, Pat. No. 5,330,471, each is a continuation-in-part of Ser. No. 711,920, Jun. 7, 1991, abandoned.

[51] Int. Cl.⁶ ................................ A61B 17/39
[52] U.S. Cl. ................... 606/48; 606/47; 606/51; 606/41
[58] Field of Search .................. 606/40, 42, 45, 606/52, 205, 209

[56] References Cited

U.S. PATENT DOCUMENTS

| | | |
|---|---|---|
| 659,409 | 9/1900 | Mosher . |
| 1,586,645 | 6/1926 | Bierman . |
| 1,798,902 | 3/1931 | Raney . |
| 3,651,811 | 3/1972 | Hiltebrandt et al. ............ 606/51 |
| 3,685,518 | 8/1972 | Beurle . |
| 3,730,188 | 5/1973 | Ellman . |
| 3,920,021 | 11/1975 | Hiltebrandt ............ 606/51 |
| 4,003,380 | 1/1977 | Wien . |
| 4,092,986 | 6/1978 | Schneiderman . |
| 4,128,099 | 12/1978 | Bauer et al. . |
| 4,232,676 | 11/1980 | Herczog . |
| 4,271,838 | 6/1981 | Lasner et al. ............ 606/147 |
| 4,353,371 | 10/1982 | Cosman . |
| 4,370,980 | 2/1983 | Lottick . |
| 4,492,231 | 1/1985 | Auth ............ 606/40 |
| 4,590,934 | 5/1986 | Malis et al. . |
| 4,601,939 | 7/1986 | Gati et al. ............ 428/161 |
| 4,643,190 | 2/1987 | Heimberger . |
| 4,655,216 | 4/1987 | Tischer . |
| 4,669,471 | 6/1987 | Hayashi . |
| 4,671,274 | 6/1987 | Sorochenko . |
| 4,763,669 | 8/1988 | Jaeger ............ 128/751 |
| 4,784,807 | 11/1988 | Blanch . |
| 4,819,633 | 4/1989 | Bauer et al. . |

(List continued on next page.)

FOREIGN PATENT DOCUMENTS

| | | |
|---|---|---|
| 2355521 | 1/1978 | France . |
| 342617 | 7/1972 | U.S.S.R. . |
| 575103 | 10/1977 | U.S.S.R. . |
| 2037167 | 7/1980 | United Kingdom . |
| 2066104 | 7/1981 | United Kingdom . |
| 2133290 | 7/1984 | United Kingdom . |
| 2161082 | 1/1986 | United Kingdom . |

OTHER PUBLICATIONS

J. D. K. Burton, *The Lancet*, "New Inventions" pp. 650–651, Oct. 24, 1959.

S. L. Corson, "Two New Laparoscopic Instruments: Bipolar Sterilizing Forceps And Uterine Manipulator", *Medical Instrumentation*, Jan.–Feb. 1977.

The Cavitron Bipolar Coagulator, Cavitron Surgical Systems, 1979.

*Primary Examiner*—Stephen C. Pellegrino
*Assistant Examiner*—Michael Peffley
*Attorney, Agent, or Firm*—Fish & Neave; Nicola A. Pisano

[57] ABSTRACT

Bipolar surgical instruments for simultaneously cutting and coagulating tissue are provided that feature increased manufacturability and durability, reduced component cost and reduced assembly requirements. The bipolar instruments include opposite polarity electrodes isolated by a layer of electrical insulation deposited and specially prepared to reduce electrical breakdown and increase smoothness. A pivot pin connecting the electrodes is impregnated with hydrophobic material, and organic materials are generally avoided in the components and manufacture of the instruments. A simplified design for an endoscopic bipolar instrument is also provided to reduce cost and improve manufacturability and durability of such devices.

18 Claims, 5 Drawing Sheets

U.S. PATENT DOCUMENTS

| | | | |
|---|---|---|---|
| 4,848,337 | 7/1989 | Shaw et al. | |
| 4,887,612 | 12/1989 | Esser et al. | 128/751 |
| 4,940,468 | 7/1990 | Petillo | 604/22 |
| 4,944,093 | 7/1990 | Falk | 30/251 |
| 4,969,885 | 11/1990 | Farin | 606/38 |
| 4,977,900 | 12/1990 | Fehling | 128/751 |
| 4,985,030 | 1/1991 | Melzer et al. | 606/31 |
| 5,009,656 | 4/1991 | Reimels | 606/48 |
| 5,085,659 | 2/1992 | Rydell | 606/47 |
| 5,108,391 | 4/1992 | Flachenecker et al. | 606/38 |
| 5,116,332 | 5/1992 | Lottick | 606/52 |
| 5,147,357 | 9/1992 | Rose et al. | 606/49 |
| 5,151,102 | 9/1992 | Kamiyama et al. | 606/51 |
| 5,324,289 | 6/1994 | Eggers | 606/48 |
| 5,330,471 | 7/1994 | Eggers | 606/48 |
| 5,391,166 | 2/1995 | Eggers | 606/49 |

BI-POLAR ELECTROSURGICAL INSTRUMENTS AND METHODS OF MAKING

This application is a continuation-in-part of commonly assigned and U.S. patent applications Ser. Nos. 07/877,703 and 07/877,704, both filed May 1, 1992, now U.S. Pat. Nos. 5,324,289, issued Jun. 28, 1994 and 5,330,471, issued Jul. 19, 1994, respectively, which are continuation-in-part applications of U.S. patent application Ser. No. 07/711,920, filed Jun. 7, 1991, abandoned.

This invention relates to improvements in hemostatic bipolar electrosurgical instruments.

BACKGROUND OF THE INVENTION

Hemostatic bipolar electrosurgical instruments which both manipulate, or sever, and coagulate tissue are described in copending and commonly assigned U.S. patent applications Ser. Nos. 07/877,703 and 07/877,704, both filed May 1, 1992, now U.S. Pat. Nos. 5,324,289 and 5,330,471, respectively. The text of those patents is incorporated herein by reference in their entirety.

The bipolar electrosurgical instruments described in the above patents have been well received in the medical community. Nevertheless, certain features of the instruments described in those patents have been found to present potential obstacles for mass production of these instruments. For example, the relatively tight tolerances required for the sliding electrical contacts employed in the endoscopic devices described in U.S. patent application Ser. No. 07/877,704, now U.S. Pat. No. 5,330,471, have been recognized to present potential cost problems when manufactured on a large scale.

It would therefore be desirable to provide improvements in both the structure and methods of making bipolar electrosurgical instruments, for use in endoscopic and open surgery, which improve the manufacturability and durability of the bipolar instruments of the type described in the above-incorporated patents.

SUMMARY OF THE INVENTION

In view of the foregoing, it is an object of the present invention to provide improved bipolar electrosurgical instruments for use in endoscopic and open surgical procedures, and methods of making such instruments, which will improve the manufacturability and durability of such devices.

It is, therefore, an object of this invention to provide improvements to the structure of the bipolar electrosurgical instruments described in the above-incorporated patents to improve manufacturability.

It is another object of this invention to provide methods of making improved bipolar electrosurgical instruments which increase the durability of such instruments.

These and other objects are accomplished in accordance with the principles of the present invention by providing bipolar electrosurgical instruments having simplified structures which are manufactured using improved manufacturing techniques. The techniques of the present invention include: 1) methods of deposition and surface preparation of insulative ceramic coatings; 2) impregnation of insulative pivot pins with electrically insulative hydrophobic material; 3) elimination of the use of organic insulation materials; 4) reduction of sharp corners on moving elements to improve insulation uniformity and durability; 5) elimination of sliding contacts in endoscopic instruments and use of low-cost injection molded parts; 6) use of hardened coatings on uninsulated shearing faces; and 7) forming of the cutting edges and tissue grasping edges to certain preferred angles.

The foregoing methods and improvements, when implemented in the open-surgery and endoscopic bipolar scissors described in copending and commonly assigned U.S. patent applications Ser. Nos. 07/877,703 and 07/877,704, both filed May 1, 1992, now U.S. Pat. Nos. 5,324,289 and 5,330,471, have been found to enhance manufacturability of such instruments, to reduce both component and assembly costs, and to provide more durable products.

BRIEF DESCRIPTION OF THE DRAWINGS

The above and other objects and advantages of the invention will be apparent upon consideration of the following detailed description, taken in conjunction with the accompanying drawings, in which like reference numerals refer to like parts throughout, and in which.

DETAILED DESCRIPTION OF THE INVENTION

The present invention is best understood in the context of the bipolar electrosurgical instruments described in copending and commonly assigned U.S. patent applications Ser. Nos. 07/877,703, now U.S. Pat. No. 5,324,289, and 07/877,704, now U.S. Pat. No. 5,330,471, which are incorporated herein by reference. The following detailed description of the present invention is set forth by briefly describing the instruments set forth in the above-incorporated patents, followed by a description of the specific improvements developed for use in those devices.

Open Surgery Bipolar Scissors

Figure 1:
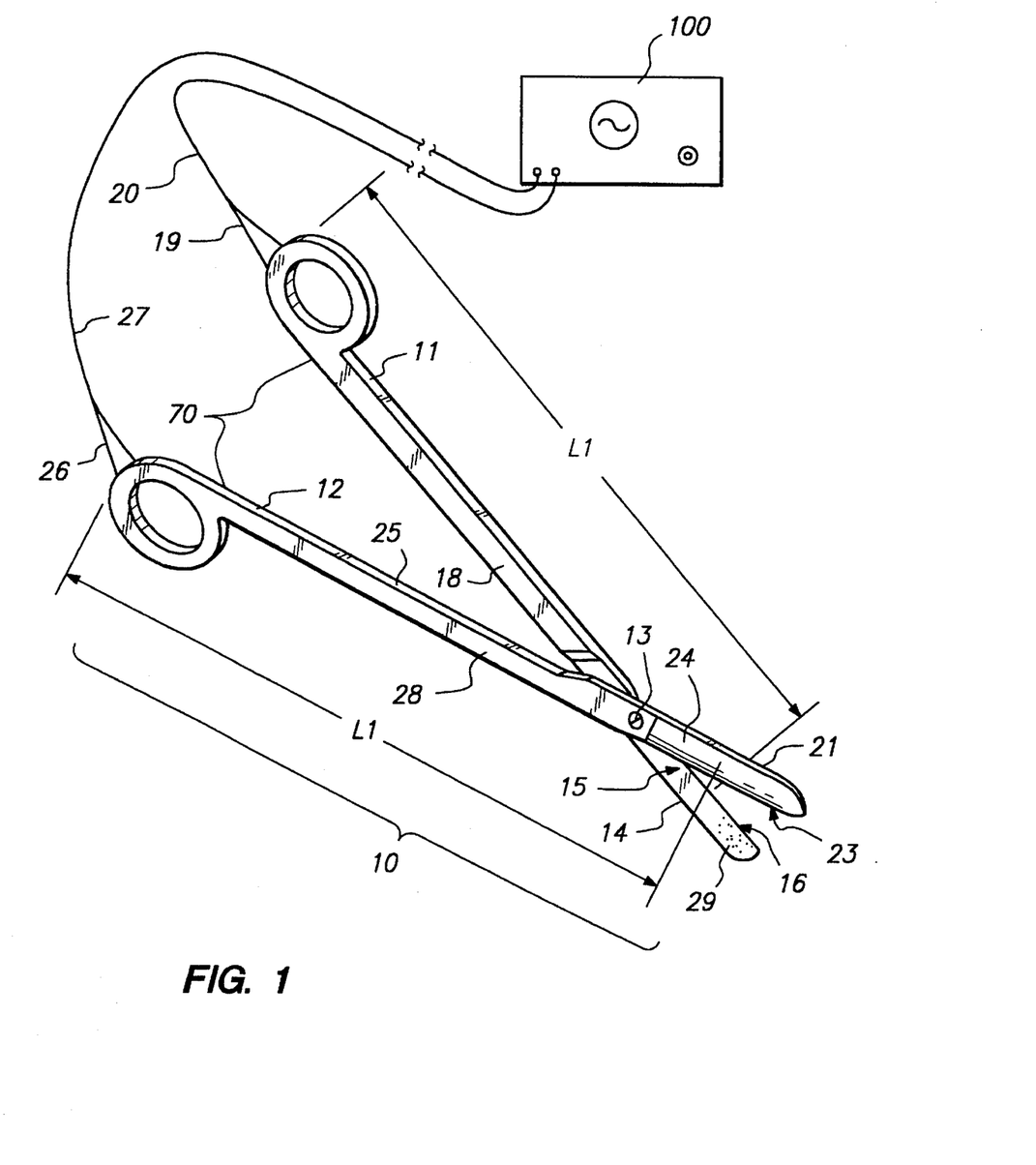
FIG. 1 is an elevated perspective view of an illustrative embodiment of an open-surgery scissor constructed in accordance with the present invention.

Referring to FIG. 1, bipolar electrosurgical scissors 10 for cutting and cauterizing a patient's tissue are shown as illustratively implementing the manufacturing methods of the present invention. Scissors 10 of FIG. 1 are constructed as described in copending and commonly assigned U.S. patent application 07/877,703, now U.S. Pat. No. 5,324,289, which is incorporated herein in its entirety, except as described hereinbelow.

Scissors 10 includes first scissor half 11 and second scissor half 12 pivotally connected by fastener 13. In one type of scissor described in the above patent, scissor half 11 is made of an electrically conducting material and has at one end a first shearing member 14. Shearing member 14 forms a first electrode comprising shearing surface 15, cutting edge 16 and exterior surface 17 (17 is not visible in FIG. 1). Scissor half 11 has, at the other end, support member 18, preferably configured with a thumb or finger hole for manipulating scissors half 11, and electrical connection 19 which connects the electrode to a power supply 100 via cable 20.

Scissor half 12 is likewise made of an electrically conducting material and has at one end shearing member 21 that forms a second electrode, shearing surface 22 (22 is not visible in FIG. 1), cutting edge 23 and exterior surface 24. Scissors half 12 likewise includes support member 25 and electrical connection 26 which connects to power supply 100 via cable 27.

Scissor halves 11 and 12 are preferably made of a rigid, structural material capable of sustaining sharp scissors-like cutting edges 16 and 23, such as stainless steel or martensitic stainless steel. Alternatively, materials of high electrical and thermal conductivity, and structurally strong enough for shearing tissue, such as copper or copper alloys, may be used. Halves 11 and 12 are pivotally connected by fastener 13 in opposition so that shearing surfaces 15 and 22 and cutting edges 16 and 23 of the shearing members move in scissors-like opposition through a range of motion to sever tissue placed therebetween.

Fastener 13 may be, for example, a screw or a rivet that electrically insulates scissor halves 11 and 12 at the pivot point. The fastener may be made of an insulative material, for example, ceramic, polyamide or nylon. Alternatively, fastener 13 may comprise a combination of non-insulative and insulative materials, such as a stainless steel screw insulated from one or both scissor halves 11 and 12 by an electrically insulative bushing (e.g., nylon or ceramic). Alternatively, fastener 13 may comprise an electrically non-insulative material, for example, aluminum, covered with an electrically insulative layer, for example, an anodized aluminum surface.

Scissor support members 18 and 25 have insulative coating 28 in regions $L_1$ to electrically insulate the support members from each other and from the surgeon using scissors 10. Insulative coating 28, which may comprise polyvinyl chloride, nylon, or other plastic insulative material, also may be applied to those areas of scissors 10 not used for cutting tissue.

A thin layer 29 of an electrically insulative material is disposed on one or both of shearing surfaces 15 and 22 to cover at least as much of those shearing surfaces as could contact the other within the full range of motion of scissor halves 11 and 12. Insulative layer 29 forms either, or both, of cutting edges 16 and 23 so that the cutting edges are electrically inactive and non-conducting. Layer 29 has a thickness (or combined thickness, if disposed on both shearing surfaces) in a range of 0.002 inches to about 0.050 inches, and more preferably 0.003 to 0.007 inches.

Insulative layer 29 allows the scissor halves forming the bipolar electrodes to move relative to each other so that current flows between exterior surface 17 of shearing member 14 and exterior surface 24 of shearing member 21, while ensuring that scissor halves 11 and 12 do not electrically contact each other. This configuration enables the cutting edges to contact each other to sever tissue while preventing short circuiting, which would impede simultaneous coagulation of the blood vessels extending through the tissue. Insulative layer 29 substantially prevents current flow directly between opposing shearing surfaces 15 and 22 when the scissor halves are closed together. Rather, the current flows through the path of least resistance between the electrodes, i.e., through the tissue in direct contact with the regions of exterior surfaces 17 and 22 adjacent to the cutting edges 16 and 23, respectively.

As described in the above-incorporated U.S. Pat. No. 5,324,289, electrically insulative layer 29 may comprise a material having a hardness that is greater or substantially greater than opposing scissor blade member. For example, shearing members 14 and 21 may be made of a martensitic stainless steel, e.g., AISI 420, while insulative layer 29 comprises an inorganic electrically insulative material such as a glass, ceramic (e.g., oxide, nitride or boride) or synthetic diamond. Thus, as layer 29 disposed on shearing surface 14 (as shown in FIG. 1) rubs against the cutting edge 23 or shearing surface 22 of shearing member 21, cutting edge 16 may be sharpened by the harder insulative material 29.

Endoscopic Bipolar Instruments

Figure 2:
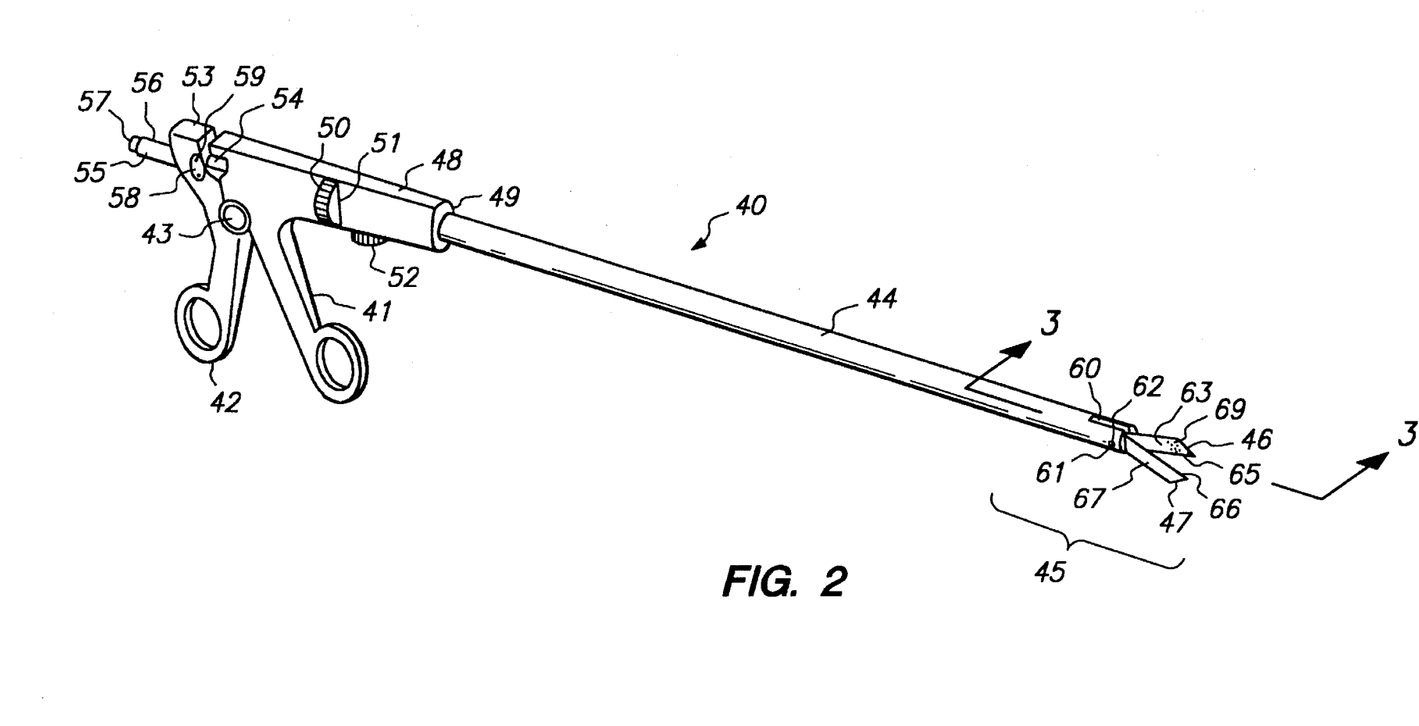
FIG. 2 is an elevated perspective view of an illustrative embodiment of an endoscopic instrument constructed in accordance with the present invention.

Referring now to FIG. 2, an illustrative bipolar endoscopic scissor, such as described in copending and commonly assigned U.S. patent application Ser. No. 07/877,704, now U.S. Pat. No. 5,330,471, is described as implementing the improvements of the present invention.

Instrument 40 includes actuating means comprising handle members 41 and 42 joined for relative movement at pivot 43, tubular elongated barrel 44, and working end 45. A drive rod disposed in elongated barrel 44 has electrical terminals that are connected to movable members 46 and 47 of working end 45 to provide an electrical potential therebetween. As described in the above-incorporated patent, movable members 46 and 47 may comprise either scissor blades or grasper members.

Handle member 41 has a pistol-like configuration, including a body portion 48 having a longitudinal bore 49 and a portion defining a hole for one or more fingers. Handle member 41 may be made of a light-weight rigid material, for example cast aluminum or injection molded plastic. Elongated barrel 44 comprises a tube having a proximal end mounted in body portion 48 and a distal portion forming part of working end 45. The proximal end of elongated barrel 44 is mounted in bore 49 of body portion 41 so that elongated barrel 44 can be rotated about its longitudinal axis. Elongated barrel may consist of a rigid structural material, for example a stainless steel alloy, e.g., SS 304, and may include a coating of electrically insulative material, such as Teflon, on its exterior surface.

Knurled rotation knob 50 is mounted on a portion of elongated barrel 44 disposed in body portion 49, so that it projects through slots 51 intersecting bore 49 of body portion 41. Rotation of knurled knob 50 causes elongated barrel 44 to rotate about its longitudinal axis, thereby also rotating working end 45. Body member 41 also has a bore communicating with bore 49 so that a set screw disposed in the bore engages elongated barrel 44 substantially perpendicularly to the longitudinal axis of the barrel. The set screw includes locking knob 52 to lock elongated barrel 44 at a desired orientation.

Handle member 42 has a lower portion defining a finger or thumb hole and an upper portion 53 having longitudinal bore 54. Longitudinal bore 54 aligns with longitudinal bore 49 in body portion 48 of handle member 41 when handle members 41 and 42 are joined for relative movement at pivot 43. Handle member 42 comprises a similar material as handle member 41, e.g., a cast aluminum alloy.

Drive rod 55 has proximal end 56 disposed within elongated barrel 44 and a distal end engaged with working end 45. Proximal end 56 of the drive rod has electrical terminals 57 projecting from its proximal endface. Drive rod 55 either comprises or is covered by an electrically insulative material to electrically isolate it from handle members 41 and 42 and elongated barrel 44 when electrical terminals 57 are connected to a power supply. Drive rod 55 includes a groove that is captured in disk 58 between pins 59. Disk 58 seats in a circular aperture in upper portion 53 of handle member 42 and is capable of angular movement in the circular aperture, when handle member 42 rotates relative to handle member 41 about pivot 43.

Scissors-like working end 45 includes diametrically opposed U-shaped slots 60 extending proximally from the distal endface of elongated barrel 44. Apertures 61 in the distal end of elongated barrel 44 are aligned across the diameter of the barrel to accept insulative pivot pin 62. As shown in FIG. 2, insulative pivot pin 62 has its ends flush with the outer surface of elongated barrel 44 and extends, from side to side, through movable members 46 and 47, and may comprise an electrically insulative metallic pin, e.g., anodized aluminum.

For the illustrative embodiment shown in FIG. 2, movable members 46 and 47 comprise scissor halves pivotally connected by insulative pivot pin 62. Movable members 46 and 47 include, respectively, shearing surfaces 63 and 64 (64 is not visible in FIG. 2), cutting edges 65 and 66, and exterior surfaces 67 and 68 (68 is not visible in FIG. 2). In one preferred embodiment of instrument 40, movable members 46 and 47 may be constructed of metallic alloys that offer good electrical conduction, adequate hardness and tensile strength sufficient to allow the members to be oriented toward each other to effect adequate wiping at the cutting edges. Suitable materials include, for example, stainless steels, martensitic stainless steels and precipitation hardened steels.

A thin layer 69 of insulative coating is provided on one or both of the opposing mating surfaces of movable members 46 and 47, including one or both of the shearing surfaces 63 and 64 to form one or both of cutting edges 65 and 66, which are electrically isolated from each other. Thus, as in instrument 10 described hereinabove, current flows between exterior surfaces 67 and 68 of movable members 46 and 47 in a region near cutting edges 65 and 66, while ensuring that movable members 46 and 47 do not electrically contact each other within the range of the cutting motion of the members. Layer 69 has a thickness (or combined thickness, if disposed on both mating surfaces) in a range of 0.002 inches to about 0.050 inches, and more preferably 0.003 to 0.007 inches.

Improvements Of The present Invention

In view of the foregoing illustrative devices, the present invention provides a number of improvements to those devices which increase manufacturability, durability and product safety. The techniques of the present invention include: 1) methods of deposition and surface preparation of insulative ceramic coatings; 2) impregnation of insulative pivot pins with electrically insulative hydrophobic material; 3) elimination of the use of organic insulation materials; 4) reduction of sharp corners on moving elements to improve insulation uniformity and durability; 5) endoscopic instrument component simplification; 6) use of hardened coatings on uninsulated shearing faces; and 7) forming of the cutting edges and tissue grasping edges to certain preferred angles.

The foregoing improvements are described seriatim hereinbelow.

1. Ceramic Insulative Layers

With respect to the bipolar scissors illustrated in FIGS. 1 and 2, insulative layer 29 of instrument 10 and insulative layer 69 of instrument 40 may be disposed on one shearing face or both shearing faces by any number of methods, for example, plasma deposition or the use of a ceramic inset bonded to the shearing face.

In conventional plasma deposition techniques, deposited material is applied at subsonic velocities. Applicants have determined, however, that by applying the insulative material, for example, aluminum oxide, at supersonic velocities, the density of the ceramic layer can be increased and the porosity of the resulting layer decreased relative to conventional methods. Applicants have developed these supersonic deposition techniques, for use in the instruments of the present invention, in cooperation with Thermal Spray Technologies, Watertown, Wis. This process is available from Thermal Spray Technologies under the tradename HVOF (High Velocity OxyFuel process).

The increased density of the ceramic layer resulting from deposition at supersonic velocities improves the smoothness of insulative layers 29 and 69, while the resulting higher density also improves the wear resistance of the layers. The reduced porosity which accompanies higher density prevents ingress of biological fluids (e.g., blood, saline) into the pores of the insulative layer, thereby improving the ability to clean and sterilize instruments 10 and 40, and thus reduce pyrogen levels between uses.

Depending upon the composition of the substrate upon which the ceramic is to be deposited, it may further be desirable to suitably prepare the substrate, for example, using a conventional bonding layer or grit blasting, to improve adhesion of the ceramic to the substrate.

In addition to increasing density of the insulative coating through improved plasma deposition techniques, applicants have found that the smoothness of the insulative layer can be further improved by post-deposition polishing. In particular, polishing the insulative layers 29 and 69 with a fine grit polishing wheel, for example, the Scotch-Brite buffing wheels available from Minnesota Mining & Manufacturing Company, Minneapolis, Minn., improves the smoothness of the scissors cutting action, reduces wear on the uninsulated scissors half, and further reduces ingress of biological fluids into the pores of the insulative layer.

Applicants have also determined that wear of the ceramic insulative layer can be reduced by disposing the insulative layer on only one shearing face, rather than on both shearing surfaces. In addition to reducing wear on the insulative layer 29 or 69, this technique permits the uninsulated half to be shaped to maximize cutting performance. Thus, for example, the uninsulated scissor halve may be bent as desired so that its cutting edge rubs with adequate force against the insulative layer disposed on the other scissor half. By contrast, such a tuning operation may damage the insulative layer where both shearing faces include an insulative layer.

2. Impregnation Of Pivot Pins

The illustrative embodiments of FIGS. 1 and 2 each include an insulative pivot pin, 13 and 62, respectively, that electrically insulate scissor halves 11 and 12 and movable members 46 and 47 from one another. Because the pivot pin experiences the full voltage differential across it when the instruments 10 and 40 are energized, the pivot pin must be rugged enough to withstand both high electrical duty and mechanical wear.

Applicant have determined that suitable pivot pins 13 and 62 may be made, for example, by first forming the parts using a high strength aluminum alloy, such as a 7000 series alloy, and then hard anodizing the parts to produce approximately a 2 mil thick layer of electrical insulation.

To prevent the ingress of biological fluid or saline solution into the pores of the anodized layer, the anodized layer is then impregnated with an electrically insulative, preferably hydrophobic, material, for example, Teflon. This technique of impregnating the pores of the electrically insulative pivot pin with a hydrophobic, electrically insulative material reduces the possibility of electrical shorting and the development of low resistance paths between scissor halves 11 and 12 or movable members 46 and 47.

3. Elimination of Organic Materials

Instruments 10 and 40 have been developed to avoid the use of organic materials in the composition and manufacture of the electrically operative portions of the devices, except for the impregnates used in the microscopic pores of the pivot pins.

Applicants have determined that by eliminating organic materials, the possibility of carbon tracking or arc tracking is greatly reduced. Such tracking modes can cause rapid failure of organic insulative materials when large voltage potentials are applied across thicknesses of only several tens of mils.

4. Improvements In Insulation Uniformity

As described hereinabove with respect to instrument 10, an electrically insulative coating 28 is disposed on support members 18 and 25 and those portions of the exterior surfaces 17 and 24 to insulate the scissors from the surgeon and from non-targeted areas of the patient's tissue.

In a preferred embodiment of scissors 10 having insulative coating 28 comprising an electrostatic powder coating of medical grade nylon, it has been found that reducing the sharp corners of scissor halves 11 and 12 improves the uniformity of insulative coating 28. In particular, it has been observed that when an insulative coating is deposited on scissor halves having sharp corners, the resulting coating is often too thin near such edges. This thin insulation coating can lead to insulation failure and arcing through the insulative coating when the scissors are exposed to maximum operating voltages. An unevenly thin insulation layer may also result in delamination of the coating near the sharp edges during repeated steam sterilizations.

It has been discovered that rounding the edges of 7 inch Metzenbaum scissor halves, for example, along edges 70 in FIG. 1, to a preferred minimum radius of 0.031 inches, greatly reduces problems associated with thin insulation coatings near otherwise sharp edges. This rounding of the scissor halve edges can be accomplished, for example, by grinding, or by casting the scissor halves in a suitably shaped mold. Of course, as will be readily understood, the desired minimum radius of curvature for such rounding may be influenced by the size of the scissors.

Coating 28 in FIG. 1 is, in the preferred embodiment, formed from a medical grade nylon having a thickness of between 5 and 15 mils. This material, when used in conjunction with a preferred minimum radius of curvature of 0.031 inches or more, has been found to provide satisfactory performance. Insulative coating 28 may in addition cover exteriors 17 and 24 of the scissor halves except for a region within 0.5 to 1.0 inches of the tip of the scissors adjacent to cutting edges 16 and 23, to avoid unwanted heating of tissue except where coagulation is desired.

5. Endoscopic Scissor Component Simplification

Endoscopic instruments such as that illustrated in FIG. 2 had, as described in copending U.S. application No. 07/877, 704, now U.S. Pat. No. 5,330,471, required the manufacture and assembly of a number of components. The sliding electrical contacts described in that application require tight control of component tolerances and careful adjustment of the assembled unit to ensure that while sliding contact is made, the frictional forces required to actuate the movable members is not excessively high. Such tight tolerancing and adjustment of the components is costly and impedes large scale manufacture and assembly. To reduce the foregoing problems, applicants sought to reduce both the number of components used in the working end, as well as the cost (and tolerances) required on such components.

Figure 3:
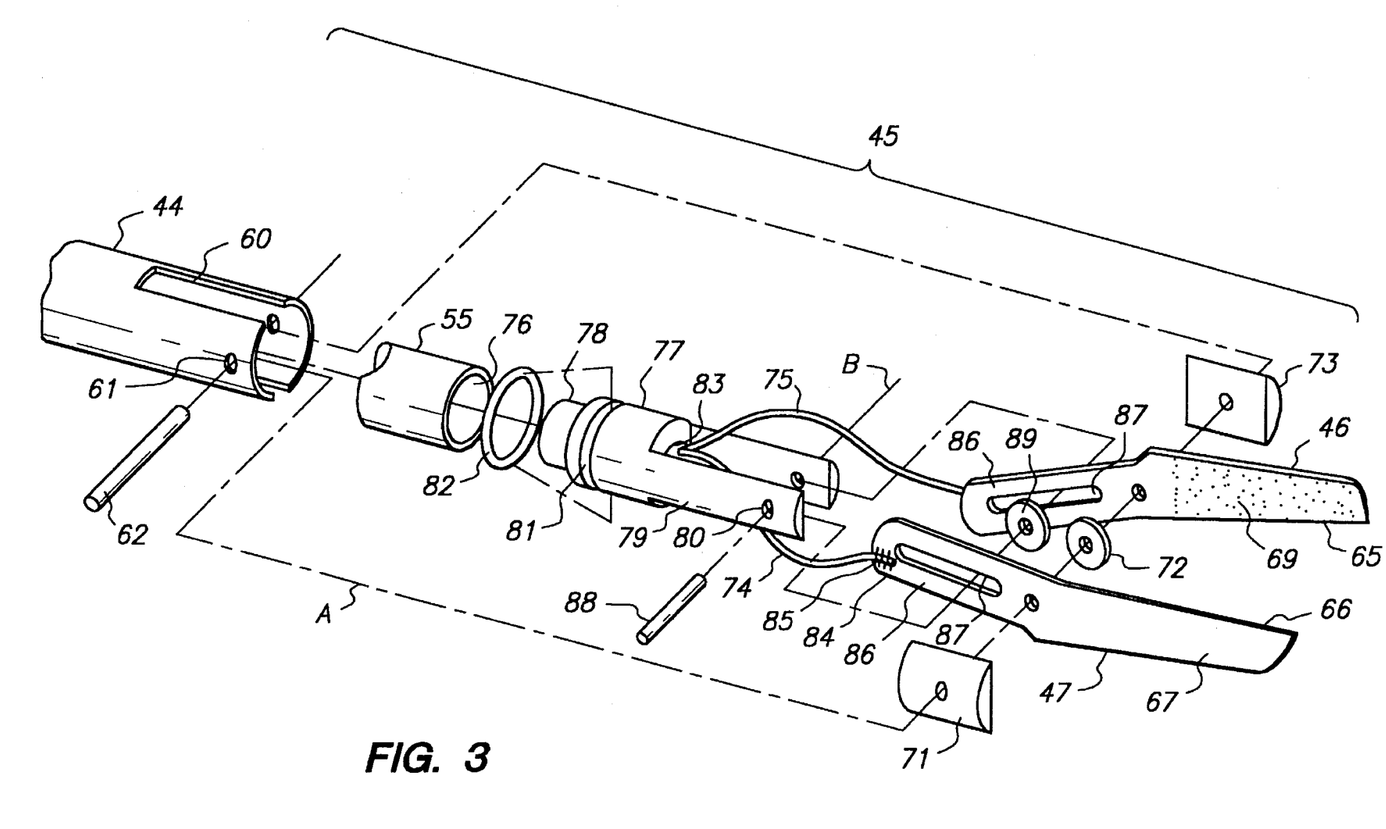
FIG. 3 is an exploded perspective view of an endoscopic instrument drive rod and scissor assembly constructed in accordance with the present invention.

Referring now to FIG. 3, the internal structure of working end 45 of endoscopic instrument 40 is described. Working end 45 of instrument 40 includes the distal end of elongated tube 44 having opposing U-shaped shaped slots 60, apertures 61 and insulative pivot pin 62. Insulative pivot pin 62 extends through a first aperture 61, a first tube insulator half, movable member 47, insulative washer 72, movable member 46, a second tube insulator half 73, and a second aperture 61, as indicated by dotted line A. Tube insulator halves 71 and 73 are disposed adjacent to the exterior surfaces of movable members 46 and 47 to electrically insulate those members from elongated barrel 44.

Insulative washer 72 may comprise, for example, an anodized aluminum washer. Use of insulative washer 72 permits the use of an insulative layer only on the proximal portion of the shearing surface, obviating the need to coat the pivot and shank regions of that scissor half. It has been determined that by reducing the size of the region that is covered by ceramic 69, the cost of applying ceramic, the potential for unwanted deformation or distortion during the coating process, and the frictional forces developed when actuating the scissor halves are all reduced.

Still referring to FIG. 3, drive rod 55 of the present invention may be composed of a sturdy, lightweight material, such as extruded plastic, and contains a central bore in which electrical leads 74 and 75 are disposed. Electrical leads 74 and 75 comprise conventional insulation-coated flexible wires (e.g., 3–10 mils in diameter) that extend to the proximal portion of instrument 40 where they are connected to electrical terminals 57. Drive rod 55 includes counterbore 76 at its distal end for accepting plug 78 of clevis member 77.

Clevis member 77 is composed of a sturdy electrically insulative material, for example, an injection molded inorganic plastic, and includes arms 79 having apertures 80. Clevis member 77 also has formed on its outer surface groove 81 in which O-ring 82 is disposed. Clevis member 77 has central bore 83 through which electrical leads 74 and 75 extend, and which is filled with a suitable potting material, for example, epoxy. Elastomeric O-ring 82 and the potting material surrounding electrical leads 74 and 75 reduce the ingress of liquids (e.g., saline, blood) into the more proximal portions of instrument 40 and also reduce the loss of pressurizing gas (e.g., carbon dioxide) commonly used during laparoscopic procedures.

Clevis member 77 replaces a number of high tolerance metal and composite structures with a single component, which may be advantageously formed using conventional injection molding processes. The electrical sliding contact of the type described in the above-mentioned patent is instead replaced by direct connection 84 of the wires of electrical leads 74 and 75 to the movable members 46 and 47 using conventional lead fastening techniques, such as swaging, crimping, welding, brazing, soldering, staking or electrically conductive adhesive. In addition, movable members 46 and 47 may include slot 85 for receiving the bare wire portions of the electrical leads, and which can be mechanically deformed to capture the wire.

Movable members 46 and 47 have shank portions 86 that include angled slots 87. Insulative drive pin 88 extends through a first aperture 80 of arm 79 of clevis member 77, first slot 87 of first shank portion 86, insulative washer 89, second slot 87 of second shank portion 86, and aperture 80 of second arm 79, as indicated by dotted line B. The ends of insulative drive pin 88 are disposed in apertures 80 of arms 79 so that they do not interfere with reciprocatory movement of drive rod 55 and clevis member 77 in elongated barrel 44.

Insulative drive pin 88 may be comprised of, for example, silicon nitride, zirconia, alumina, or other material which has the mechanical strength to withstand the loads imposed on the pins during opening and closing of movable members 46 and 47, while providing the requisite electrical insulation between shank portions 86. Insulative drive pin 88 may comprise an anodized aluminum pin as described hereinabove. Insulative washer 89 may also comprise an anodized aluminum washer and obviates the need for insulating shank portions 86, as described in the above-mentioned patent.

Slots 87 are configured so that when the handle members are actuated to urge drive rod 55 in a distal direction, insulative drive pin 88 is urged to the distal ends of slots 87, thereby opening movable members 46 and 47. In this first position, working end 45 may be positioned so that members 46 and 47 are located proximate to the tissue, without imposing any mechanical load thereon. On the other hand, when handle member 42 is rotated towards handle member 41, drive rod 55 is reciprocated proximally. This motion pulls drive pin 88 toward to the proximal ends of slots 87, thereby closing movable members 46 and 47. As movable members 46 and 47 are gradually closed, the cutting point defined by the intersection of cutting edges 65 and 66, moves along those cutting edges, so that a current flows through the tissue to cause hemostasis of the tissue immediately prior to its being severed mechanically. Thus, in this second position, hemostasis is achieved in the tissue by the current flowing between members 46 and 47, and then mechanically severed.

The above-described preferred embodiment of working end 45 significantly reduces the cost of drive rod 55, significantly reduces the component cost, the labor required for assembly and adjustment of the instrument, offers increased production yields, and reduces the frictional forces associated with actuating the movable members. The use of O-ring 82 as described in the above embodiment also reduces ingress of biological fluids into instrument 40 and assists in reducing the escape of pressurizing gases from the operative site.

6. Use Of Hardened Coatings On Uninsulated Surfaces

It has been determined that the high hardness of a ceramic insulated scissor half can result in high rates of wear of an uninsulated opposing shearing member. In the preferred embodiment, it has been found to be advantageous to coat the uninsulated scissors half with a coating of high hardness material (hardness equal to or greater than 70 Rockwell C scale), for example, chromium carbide, to improve the wear resistance of the scissor half that does not carry the ceramic coating or inset.

This aspect of the preferred embodiment of the present invention has applicability to both open surgery instruments such as instrument 10, as well as endoscopic devices, such as instrument 40.

7. Forming Of Cutting And Grasping Edges

Figure 4:
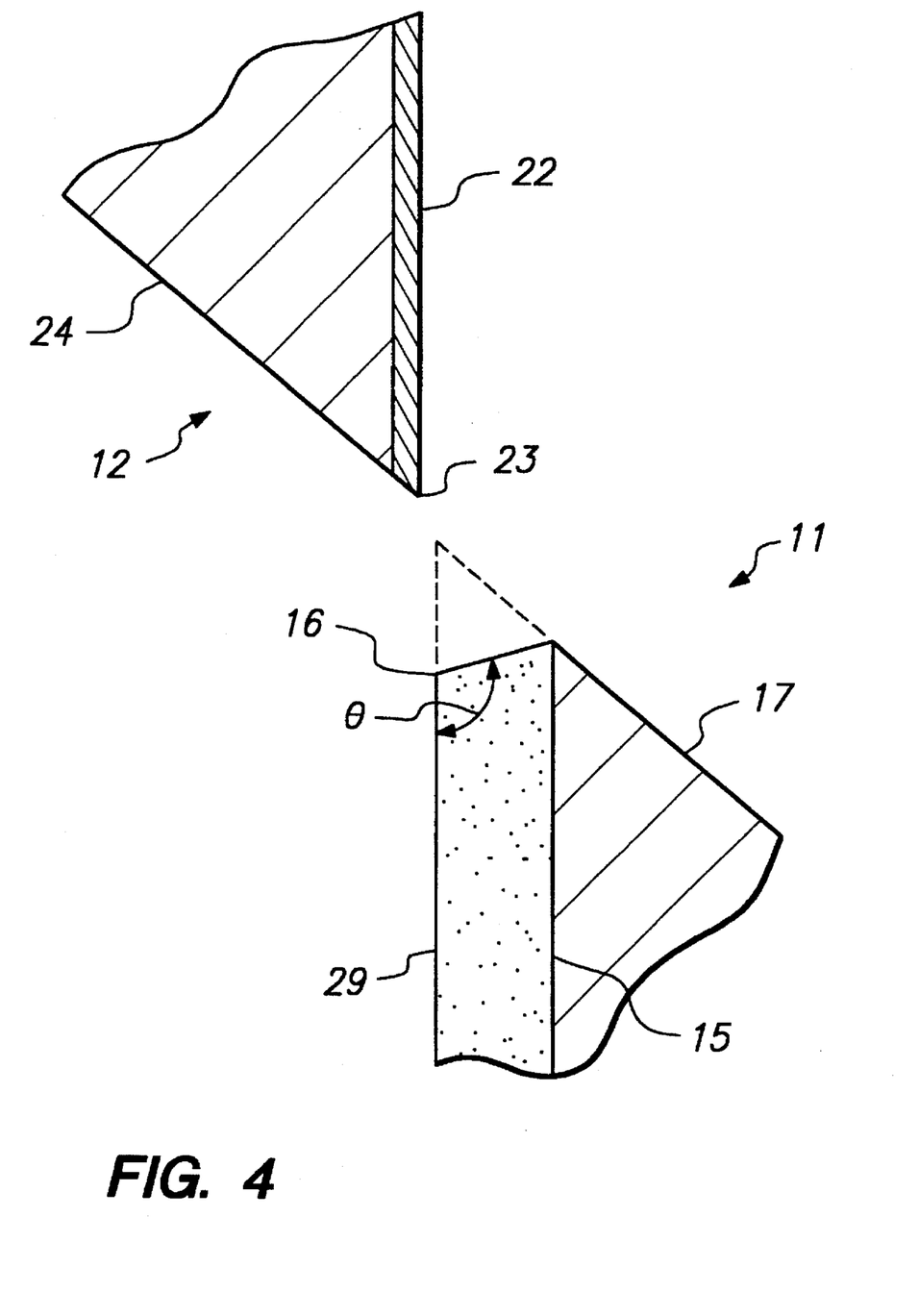
FIG. 4 is a partial cross-sectional view of a scissor blade showing the included angle of the insulation layer.

Referring to FIGS. 1 and 4, this aspect of the present invention is described with respect to cutting edges 16 and 23 of scissor halves 11 and 12. It will be readily understood, of course, that this aspect of the present invention is equally applicable to the cutting edges of movable members 46 and 47 of working end 45.

It has been observed that when the included angle Θ of ceramic layer 29 forms less than a 90° degree angle to the slope of exterior surface 17 of cutting edge 16 (as shown in dotted line), ceramic layer 29 may experience undesirable chipping and may impose excessive wear of the opposing non-ceramic cutting edge 23 and shearing face 22. Coating shearing face 22 with an optional high hardness coating may reduce wear of the surface and cutting edge, as described above.

Applicants have determined that undesirable chipping of ceramic cutting edge 16 can be reduced by increasing included angle Θ so that it exceeds 90° by a few degrees. This included angle can be obtained by a grinding or honing process for deposited ceramic coatings, or could be a feature of the mold used to form a ceramic inset for the scissor half. Use of an included angle exceeding 90° provides an angle which is large enough to reduce chipping and wear while still being sufficiently small to provide good surgical cutting performance.

Figures 5A, 5B:
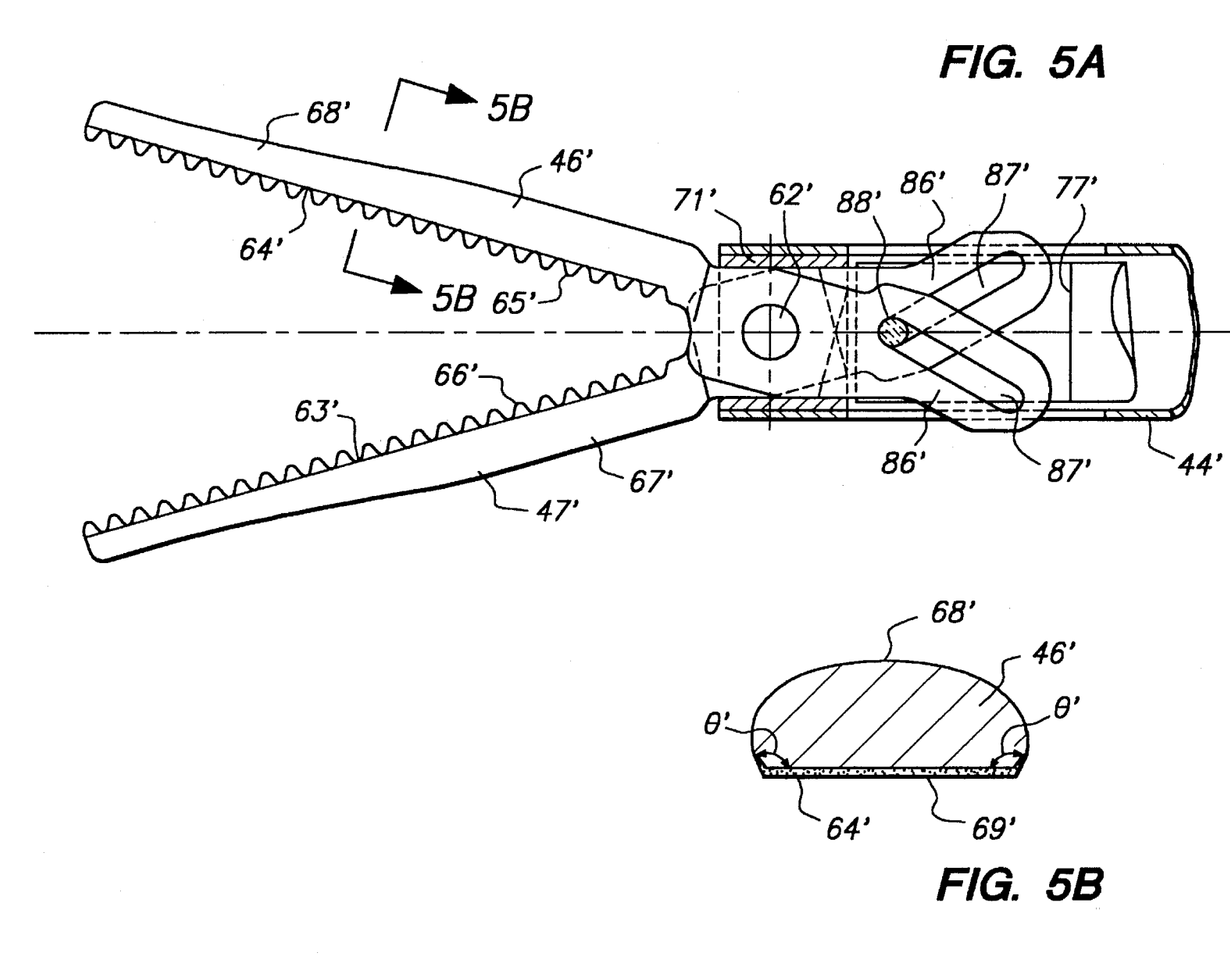
FIGS. 5A and 5B are sectional views of a chamfered graspers constructed in accordance with the present invention.

Referring now to FIGS. 5A and 5B, the graspers embodiment of the instrument described in U.S. patent application Ser. No. 07/877,704, now U.S. Pat. No. 5,330,471, is illustrated as constructed in accordance with the present invention. In this alternative embodiment of working end 45 of instrument 40, like-primed numbers designate similar elements.

Jaw-like members 46' and 47' have shank portions 86' including slots 87'. Insulated drive pin 88' extends through slots 87' and has its ends secured in apertures 80' of clevis member 77'. Members 46' and 47' have grasping surfaces 63' and 64', teeth 65' and 66', and exterior surfaces 67' and 68', respectively. Teeth 65' and 66' are disposed in opposing relation on grasping surfaces 63' and 64' to grasp tissue captured between members 46' and 47'.

A thin layer 69' of insulative material covers the opposing surfaces of teeth 65' and 66' of the respective members. Alternatively, teeth 65' and 66' may be dimensioned so that when the members are in the closed position, a gap exists between the teeth sufficient to prevent direct shorting between the members. Insulative washers (not shown) are disposed on insulative drive pin 88' and pivot pin 62' to electrically insulate members 46' and 47' from each other.

In accordance with this aspect of the present invention, members 46' and 47' are formed so that the included angle Θ' formed by the grasping surface 64' and exterior surface 68' exceeds 90°. Applicants have determined that formation of included angle Θ' at a preferred value of 135° significantly reduces sticking of tissue to grasper surfaces 63' and 64'. Members 46' and 47' may be shaped to the preferred included angle by any suitable means, for example, grinding or design of a suitably shaped casting mold.

The various embodiments described herein are presented for purposes of illustration and not limitation, as the present invention can be practiced with surgical instruments of any type having two electrically insulated pivoted opposing members. One skilled in the art will appreciate that the present invention can be practiced by other than the described embodiments, and that the present invention is limited only by the claims that follow.

What is claimed is:

1. An instrument for hemostatically cutting tissue by passing a current therethrough, the instrument comprising:
    a first and second shearing members having first and second shearing surfaces, first and second cutting edges and first and second electrodes located adjacent to the first and second cutting edges, respectively, each of the first and second cutting edges having a length;
    a layer of electrically insulative material disposed on at least one of the first and second shearing members to form the substantially the entire length of one of the first and second cutting edges; and a pin pivotally joining the first and second shearing members so that the first shearing member moves relative to the second shearing member in a scissors-like cutting motion wherein the first and second shearing members close together to sever tissue located therebetween and so that a current flows between the first and second shearing members through the tissue to cause hemostasis thereof, wherein the insulative layer disposed on at least one of the first and second shearing members is deposited, by plasma deposition at supersonic velocities.

2. An instrument as defined in claim 1 wherein none of the first and second shearing members, insulative layer and pivot pin employ an organic material.

3. An instrument for hemostatically cutting tissue by passing a current therethrough, the instrument comprising:

a first and second shearing members having first and second shearing surfaces, first and second cutting edges and first and second electrodes located adjacent to the first and second cutting edges, respectively, each of the first and second cutting edges having a length;

a layer of electrically insulative material disposed on at least one of the first and second shearing members to form substantially the entire length of one of the first and second cutting edges;

a pin pivotally joining the first and second shearing members so that the first shearing member moves relative to the second shearing member in a scissors-like cutting motion wherein the first and second shearing members close together to sever tissue located therebetween and so that a current flows between the first and second shearing members through the tissue to cause hemostasis thereof; and an insulative washer disposed on the pivot pin to electrically insulate the first and second shearing members from one another adjacent to the pivot pin.

4. An instrument as defined in claim 3 wherein none of the first and second shearing members, insulative layer and pivot pin employ an organic material.

5. An instrument for hemostatically cutting tissue by passing a current therethrough, the instrument comprising:

a first and second shearing members having first and second shearing surfaces, first and second cutting edges and first and second electrodes located adjacent to the first and second cutting edges, respectively, each of the first and second cutting edges having a length;

a layer of a first electrically insulative material disposed on at least one of the first and second shearing members to form the substantially the entire length of one of the first and second cutting edges; and a pin pivotally joining the first and second shearing members so that the first shearing member moves relative to the second shearing member in a scissors-like cutting motion wherein the first and second shearing members close together to sever tissue located therebetween and so that a current flows between the first and second shearing members through the tissue to cause hemostasis thereof, wherein the pivot pin is impregnated with a second electrically insulative material.

6. An instrument as defined in claim 4 wherein the second electrically insulative material is hydrophobic.

7. An instrument for hemostatically cutting tissue by passing a current therethrough, the instrument comprising:

a first and second shearing members having first and second shearing surfaces, first and second cutting edges and first and second electrodes located adjacent to the first and second cutting edges, respectively, each of the first and second cutting edges having a length;

a layer of a first electrically insulative material disposed on at least one of the first and second shearing members to form the substantially the entire length of one of the first and second cutting edges; and a pin pivotally joining the first and second shearing members so that the first shearing member moves relative to the second shearing member in a scissors-like cutting motion wherein the first and second shearing members close together to sever tissue located therebetween and so that a current flows between the first and second shearing members through the tissue to cause hemostasis thereof, wherein the first shearing member further comprises a first support member and the second shearing member further comprises a second support member, the first and second support members having radiused edges, the first and second support members having a coating of a second electrically insulative material disposed thereon.

8. An instrument as defined in claim 7 wherein the coating of the second electrically insulative material comprises nylon having a thickness in a range of 5 to 15 mils.

9. An instrument for hemostatically cutting tissue by passing a current therethrough, the instrument comprising:

an elongated barrel having a proximal end and a distal end, the elongated barrel having a bore;

a drive rod having a bore and a distal end, the drive rod disposed within the bore for reciprocating movement;

a clevis member coupled to the distal end of the drive rod, the clevis member including a bore;

first and second shearing members disposed from the distal end of the elongated barrel, the first and second shearing members each including a shank portion having a longitudinally directed slot, the first and second shearing members having first and second shearing surfaces, first and second cutting edges and first and second electrodes located adjacent to the first and second cutting edges, respectively, each of the first and second cutting edges having a length;

first and second electrical leads disposed in the bore of the drive rod and the bore of the clevis member, the first and second leads electrically coupled to the first and second electrodes;

a layer of electrically insulative material disposed on at least one of the first and second shearing members to form the substantially the entire length of one of the first and second cutting edges;

a drive pin mounted in the clevis member and extending through the slots in the shank portions and adapted for reciprocation in proximal and distal directions;

a pivot pin mounted in the elongated tube and pivotally joining the first and second shearing members so that the first shearing member moves relative to the second shearing member in a scissors-like cutting motion wherein the first and second shearing members close together to sever tissue located therebetween and so that a current flows between the first and second shearing members through the tissue to cause hemostasis thereof; and actuating means connected to the drive rod to reciprocate the drive pin in the longitudinal slots, wherein the first and second leads are directly connected to the first and second shearing members.

10. An instrument as defined in claim 9 wherein the drive rod comprises a high strength electrically insulative plastic material.

11. An instrument as defined in claim 10 wherein the clevis member comprises an injection molded plastic component.

12. An instrument as defined in claim 11 wherein the clevis member includes a circumferential groove and the instrument further comprises an elastomeric ring captured in the groove.

13. An instrument for hemostatically cutting tissue by passing a current therethrough, the instrument comprising:

a first and second shearing members having first and second shearing surfaces, first and second cutting edges and first and second electrodes located adjacent to the first and second cutting edges, respectively, each of the first and second cutting edges having a length;

a layer of electrically insulative material disposed on the first shearing member to form the substantially the entire length of one of the first cutting edge;

a layer of high hardness electrically conductive material disposed on the second shearing member to form the second cutting edge and second shearing surface; and a pin pivotally joining the first and second shearing members so that the first shearing member moves relative to the second shearing member in a scissors-like cutting motion wherein the first and second shearing members close together to sever tissue located therebetween and So that a current flows between the first and second shearing members through the tissue to cause hemostasis thereof.

14. An instrument for hemostatically cutting tissue by passing a current therethrough, the instrument comprising:

a first and second shearing members having first and second shearing surfaces, first and second cutting edges and first and second electrodes located adjacent to the first and second cutting edges, respectively, each of the first and second cutting edges having a length;

a layer of electrically insulative material disposed on at least one of the first and second shearing members to form the substantially the entire length of one of the first and second cutting edges; and a pin pivotally joining the first and second shearing members so that the first shearing member moves relative to the second shearing member in a scissors-like cutting motion wherein the first and second shearing members close together to sever tissue located therebetween and so that a current flows between the first and second shearing members through the tissue to cause hemostasis thereof, wherein the layer of electrically insulative material defines an included angle at the cutting edge that exceeds 90°.

15. An instrument as defined in claim 14 further comprising a first insulative washer disposed on the pivot pin to electrically insulate the first and second shearing members from one another adjacent to the pivot pin.

16. An instrument as defined in claim 15 further comprising a second insulative washer disposed on the drive pin to electrically insulate the shank portions of the first and second shearing members from one another.

17. An instrument as defined in claim 16 wherein the first and second insulative washers comprise aluminum having a hard anodized surface layer.

18. An instrument for performing endoscopic electrosurgery on a tissue by passing a current through the tissue to cause hemostasis thereof, the instrument comprising:

an elongated barrel having a proximal end and a distal end;

first and second grasping members disposed on the distal end of the elongated barrel, the first grasping member having a first grasping surface, and a first exterior surface, a portion of the first exterior surface adjacent the first grasping surface defining a first electrode, the second grasping member having a second grasping surface, and a second exterior surface, a portion of the second grasping member adjacent the second grasping surface defining a second electrode;

means for connecting the first and second grasping members so that the first and second grasping surfaces move through a range of motion in a graspers-like action to grasp tissue disposed therebetween;

an electrically insulative material disposed on at least one of the first and second grasping members to form the grasping surface of that grasping member, so that the first and second electrodes do not contact each other in the range of motion, and so that the current passes between the first and second electrodes through the tissue and not between the first and second grasping surfaces; and actuating means coupled to the first and second grasping members to move the first and second grasping members through the range of motion, wherein at least one of the first grasping surface and the first exterior surface and the second grasping surface and the second exterior surface intersect at an angle exceeding 90°.

* * * * *